United States Patent [19]

Bajor et al.

[11] Patent Number: 5,773,015

[45] Date of Patent: Jun. 30, 1998

[54] METHOD FOR CONTROLLING SKIN OILS AND GREASE

[75] Inventors: John Steven Bajor, Ramsey, N.J.; Angel Augusto Guerrero, Huntington, Conn.; Helen Elizabeth Knaggs, Weehawken, N.J.

[73] Assignee: Elizabeth Arden Co., Division of Conopco, Inc., New York, N.Y.

[21] Appl. No.: 774,328

[22] Filed: Nov. 27, 1996

[51] Int. Cl.$^6$ .................................................. A61K 7/48
[52] U.S. Cl. ..................... 424/401; 424/59; 514/159; 514/844; 514/845; 514/846; 514/847
[58] Field of Search ............... 424/401, 59, 159; 514/844–847

[56] References Cited

U.S. PATENT DOCUMENTS

| | | |
|---|---|---|
| 4,891,227 | 1/1990 | Thaman et al. . |
| 4,891,228 | 1/1990 | Thaman et al. . |
| 5,262,407 | 11/1993 | Leveque et al. . |

FOREIGN PATENT DOCUMENTS

| | | |
|---|---|---|
| 0 696 194 | 3/1995 | European Pat. Off. . |
| 4-036 238 | 2/1992 | Japan . |
| WO 93/10755 | 6/1993 | WIPO . |
| WO 93/10756 | 6/1993 | WIPO . |

OTHER PUBLICATIONS

Product Brochure—Vevy Europe, BTNA (1990).
Product Brochure—Lexicon Vevy Europe, Skin Care Instant Reports (1990).
Elizabeth Arden "SPA Comeback Cream"—(1994) carton with ingredient listing including tridecyl salicylate.

*Primary Examiner*—Jyothsan Venkat
*Attorney, Agent, or Firm*—Milton L. Honig

[57] ABSTRACT

A method is provided for inhibiting oil and grease generation from human skin by applying to the skin a $C_{11}$–$C_{30}$ alkyl or alkenyl ester of salicylic acid as an active component in combination with a pharmaceutically acceptable carrier. Most preferred is tridecyl salicylate.

3 Claims, No Drawings

METHOD FOR CONTROLLING SKIN OILS AND GREASE

BACKGROUND OF THE INVENTION

1. Field of the Invention

The invention relates to a method for controlling oil and grease secretion from skin.

2. The Related Art

Sebum is produced by the disruption of the cells in which it is formed (in the basal layer of the gland). This function may be termed holocrine secretion.

Being liquid inside the duct and hair follicle, sebum diffuses up and down the follicular canal. Upon reaching the skin surface it combines with epithelial lipids (from the keratinizing cells) and emulsifies as an oily liquid with water from the sweat glands. In this way a semi-solid, slightly acid, hydrophilic film is formed on the skin and in the hair follicles. The quantity of sebum produced is directly proportional to the size of the gland.

The rate of sebum production varies in different individuals, some having oilier skins than others. Male sex hormones increase sebum production. Increased temperature also increases production.

The literature is replete with methods and compositions for eliminating, treating or at least reducing the levels of skin oils and greasiness. None have proved totally satisfactory.

Accordingly, it is an object of the present invention to provide an improved method for control of oiliness and greasiness in human skin. This and other objects of the present invention will become more fully apparent from the subsequent summary and detailed discussion.

SUMMARY OF THE INVENTION

A method for controlling oiliness and greasiness in human skin is provided which involves topical application to the skin of a safe and effective amount of salicylate ester having the formula (I):

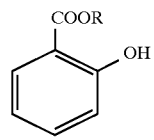
(I)

wherein R is a $C_{11}$–$C_{30}$ alkyl or alkenyl radical.

DETAILED DESCRIPTION OF THE INVENTION

Now it has been discovered that oil and grease production by skin may be controlled, reduced and inhibited through application of a cosmetic composition including as active a derivative of salicylic acid having formula (I):

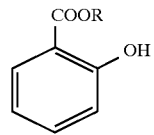
(I)

wherein R is a $C_{11}$–$C_{30}$ alkyl or alkenyl radical. Most preferred are the $C_{12}$–$C_{20}$ alkyl or alkenyl, optimally the $C_{13}$ alkyl or alkenyl esters of salicylic acid. By the term "skin" is meant to include all areas containing sebaceous glands, such as face, back, chest and scalp.

"Safe and effective amounts" of the $C_{11}$–$C_{30}$ esters of salicylic acid are to be used within cosmetic compositions of the present invention. The term "safe and effective amounts" are defined as any amount sufficient to significantly induce a positive modification in lipid production but low enough to avoid any undesirable side effects (at a reasonable benefit/risk ratio), within the scope of sound medical judgement. The safe and effective amount of the salicylate esters will vary with the particular age and physical condition of the subject being evaluated, the severity of the condition, the duration of the treatment, the nature of concurrent therapy, the specific ester employed, the particular pharmaceutically-acceptable carrier utilized, and like factors. Generally these amounts may range from 0.01 to 20%, preferably from 0.1 to 10%, more preferably from 1 to 8%, optimally from 2 to 6% by weight.

Besides the active salicylate ester, compositions of the present invention will utilize a pharmaceutically acceptable carrier. The carrier may either be aqueous, anhydrous or an emulsion. Preferably the compositions are aqueous, especially water and oil emulsions of the W/O or O/W variety. Water when present will be in amounts which may range from 5 to 95%, preferably from 20 to 70%, optimally between 35 and 60% by weight.

Besides water, relatively volatile solvents may also serve as carriers within compositions of the present invention. Most preferred are monohydric $C_1$–$C_3$ alkanols. These include ethyl alcohol, methyl alcohol and isopropyl alcohol. The amount of monohydric alkanol may range from 1 to 70%, preferably from 10 to 50%, optimally between 15 to 40% by weight.

Emollient materials may also serve as pharmaceutically acceptable carriers. These may be in the form of silicone oils and synthetic esters. Amounts of the emollients may range anywhere from 0.1 to 50%, preferably between 1 and 20% by weight.

Silicone oils may be divided into the volatile and non-volatile variety. The term "volatile" as used herein refers to those materials which have a measurable vapor pressure at ambient temperature. Volatile silicone oils are preferably chosen from cyclic or linear polydimethylsiloxanes containing from 3 to 9, preferably from 4 to 5, silicon atoms.

Linear volatile silicone materials generally have viscosities less than about 5 centistokes at 25° C. while cyclic materials typically have viscosities of less than about 10 centistokes.

Nonvolatile silicone oils useful as an emollient material include polyalkyl siloxanes, polyalkylaryl siloxanes and polyether siloxane copolymers. The essentially non-volatile polyalkyl siloxanes useful herein include, for example, polydimethyl siloxanes with viscosities of from about 5 to about 100,000 centistokes at 25° C. Among the preferred non-volatile emollients useful in the present compositions are the polydimethyl siloxanes having viscosities from about 10 to about 400 centistokes at 25° C.

Among the ester emollients are:

(1) Alkenyl or alkyl esters of fatty acids having 10 to 20 carbon atoms. Examples thereof include isoarachidyl neopentanoate, isononyl isonanonoate, oleyl myristate, oleyl stearate, and oleyl oleate.

(2) Ether-esters such as fatty acid esters of ethoxylated fatty alcohols.

(3) Polyhydric alcohol esters. Ethylene glycol mono and di-fatty acid esters, diethylene glycol mono- and di-fatty acid esters, polyethylene glycol (200–6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.

(4) Wax esters such as beeswax, spermaceti, myristyl myristate, stearyl stearate and arachidyl behenate.

(5) Sterols esters, of which cholesterol fatty acid esters are examples thereof.

Fatty acids having from 10 to 30 carbon atoms may also be included as pharmaceutically acceptable carriers for compositions of this invention. Illustrative of this category are pelargonic, lauric, myristic, palmitic, stearic, isostearic, hydroxystearic, oleic, linoleic, ricinoleic, arachidic, behenic and erucic acids.

Humectants of the polyhydric alcohol-type may also be employed as pharmaceutically acceptable carriers in compositions of this invention. The humectant aids in increasing the effectiveness of the emollient, reduces scaling, stimulates removal of built-up scale and improves skin feel. Typical polyhydric alcohols include glycerol, polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, 1,2,6-hexanetriol, ethoxylated glycerol, propoxylated glycerol and mixtures thereof. For best results the humectant is preferably propylene glycol. The amount of humectant may range anywhere from 0.5 to 30%, preferably between 1 and 15% by weight of the composition.

Thickeners may also be utilized as part of the pharmaceutically acceptable carrier of compositions according to the present invention. Typical thickeners include crosslinked acrylates (e.g. Carbopol 982®), hydrophobically-modified acrylates (e.g. Carbopol 1382®), cellulosic derivatives and natural gums. Among useful cellulosic derivatives are sodium carboxymethylcellulose, hydroxypropyl methylcellulose, hydroxypropyl cellulose, hydroxyethyl cellulose, ethyl cellulose and hydroxymethyl cellulose. Natural gums suitable for the present invention include guar, xanthan, sclerotium, carrageenan, pectin and combinations of these gums. Amounts of the thickener may range from 0.0001 to 5%, usually from 0.001 to 1%, optimally from 0.01 to 0.5% by weight.

Collectively the water, solvents, silicones, esters, fatty acids, humectants and/or thickeners will constitute the pharmaceutically acceptable carrier in amounts from 1 to 99.9%, preferably from 80 to 99% by weight.

Cosmetic compositions of the present invention may be in any form. These forms may include emulsified systems such as lotions and creams, microemulsions, roll-on formulations, mousses, ointments (hydrophilic and hydrophobic), aerosol and non-aerosol sprays and pad-applied formulations.

Surfactants may also be present in cosmetic compositions of the present invention. Total concentration of the surfactant will range from 0.1 to 40%, preferably from 1 to 20%, optimally from 1 to 5% by weight of the composition. The surfactant may be selected from the group consisting of anionic, nonionic, cationic and amphoteric actives. Particularly preferred nonionic surfactants are those with a $C_{10}-C_{20}$ fatty alcohol or acid hydrophobe condensed with from 2 to 100 moles of ethylene oxide or propylene oxide per mole of hydrophobe; $C_2-C_{10}$ alkyl phenols condensed with from 2 to 20 moles of alkylene oxide; mono- and di-fatty acid esters of ethylene glycol; fatty acid monoglyceride; sorbitan, mono- and di-$C_8-C_{20}$ fatty acids; block copolymers (ethylene oxide/propylene oxide); and polyoxyethylene sorbitan as well as combinations thereof. Alkyl polyglycosides and saccharide fatty amides (e.g. methyl gluconamides) are also suitable nonionic surfactants.

Preferred anionic surfactants include soap, alkyl ether sulfate and sulfonates, alkyl sulfates and sulfonates, alkylbenzene sulfonates, alkyl and dialkyl sulfosuccinates, $C_8-C_{20}$ acyl isethionates, acyl glutamates, $C_8-C_{20}$ alkyl ether phosphates and combinations thereof.

Sunscreen actives may also be included in compositions of the present invention. Particularly preferred are such materials as ethylhexyl p-methoxycinnamate, available as Parsol MCX, and benzophenone-3, also known as Oxybenzone. Inorganic sunscreen actives may be employed such as microfine titanium dioxide, polyethylene and various other polymers. Amounts of the sunscreen agents will generally range from 0.1 to 30%, preferably from 2 to 20%, optimally from 4 to 10% by weight.

Preservatives can desirably be incorporated into the cosmetic compositions of this invention to protect against the growth of potentially harmful microorganisms. Suitable traditional preservatives for compositions of this invention are alkyl esters of para-hydroxybenzoic acid. Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are phenoxyethanol, methyl paraben, propyl paraben, imidazolidinyl urea, sodium dehydroacetate and benzyl alcohol. The preservatives should be selected having regard for the use of the composition and possible incompatibilities between the preservatives and other ingredients in the emulsion. Preservatives are preferably employed in amounts ranging from 0.01% to 2% by weight of the composition.

Compositions of the present invention may also contain water-soluble vitamins. The term water-soluble defines substances with a solubility of at least 0.1%, preferably at least 1%, optimally at least 5% by weight in water. Illustrative water-soluble vitamins are Niacin, Vitamin $B_6$, Vitamin C and Biotin. One source for Vitamin C is a product sold under the trademark of Vitazyme C available from the Brooks Company. Niacin, Vitamin B and Biotin are available from Roche Pharmaceuticals. Total amount of vitamins in compositions according to the present invention may range from 0.001 to 1%, preferably from 0.01 to 0.6, optimally from 0.1 to 0.5% by weight.

Keratolytic agents such as $C_2-C_{25}$ α-hydroxy alkanoic acids may also be incorporated into compositions of this invention. Illustrative of this group of materials are glycolic, lactic, α-hydroxyoctanoic acids and salts thereof. The salts may be selected from alkalimetal, ammonium and $C_1-C_{20}$ alkyl or alkanolammonium counterions. Levels of α-hydroxyalkanoic acids may range from 0.001 to 10%, preferably between 0.2 and 1%, optimally between 0.4 and 0.5% by weight.

Minor adjunct ingredients may also be present in the cosmetic compositions. Among them may be the water-insoluble vitamins such as Vitamin A Palmitate, Vitamin E Acetate and DL-panthenol.

Another adjunct ingredient can be that of an enzyme. Particularly preferred is superoxide dismutase, commercially available as Biocell SOD from Brooks Industries, USA.

Natural vegetable materials from renewable resources are often desirable in cosmetic compositions. For instance, cosmetic compositions of the present invention may include p-glucan derived from oats, commercially available under the trademark Microat SF from Nurture Inc., Missoula, Mont.

Colorants, fragrances, opacifiers and abrasives may also be included in compositions of the present invention. Each of these substances may range from 0.05 to 5%, preferably between 0.1 and 3% by weight.

The following Examples will more fully illustrate embodiments of this invention. All parts, percentages and proportions referred to herein and in the appended claims are by weight unless otherwise indicated.

EXAMPLE 1

The following skin oil and grease reducing sunscreen creme is prepared having a composition described in Table I.

TABLE I

| COMPONENT | WEIGHT % |
| --- | --- |
| Carbopol 1382 ® (2% solids) | 8.000 |
| Spectron SA-13 ® (Tridecyl Salicylate) | 6.000 |
| Parsol MCX ® | 6.000 |
| Isoarachidyl Neopentanoate | 4.300 |
| Benzophenone-3 | 3.000 |
| Glycerin | 3.000 |
| Isononyl Isononanoate | 2.500 |
| Arlacel 165 VS ® (GMS/PEG) | 1.700 |
| BRIJ 721 ® (Vegetable) | 1.200 |
| Isostearic Acid | 1.200 |
| Polymethyl Methacrylate | 1.000 |
| Cetyl Alcohol | 1.000 |
| Triethanolamine | 0.770 |
| Phenoxyethanol | 0.700 |
| Actiglyde-J Special ® (Bio-hyaluronic acid) | 0.500 |
| Vitamin E Acetate | 0.500 |
| BRIJ 72 ® (Vegetable) | 0.300 |
| Methylparaben | 0.300 |
| Polyethylene (A-C 400) ® | 0.300 |
| Algae Extract | 0.250 |
| Glydant ® | 0.200 |
| DL-Panthenol | 0.200 |
| $C_{12}$–$C_{20}$ Acid-PEG 8 Esters | 0.200 |
| Trilaureth-4-Phosphate | 0.200 |
| Silicone 200 (10 cst) | 0.200 |
| Microat SF ® | 0.200 |
| Niacin | 0.200 |
| Amigel ® | 0.170 |
| Vitazyme C ® | 0.100 |
| Superoxide Dismutase | 0.100 |
| Vitamin $B_6$ | 0.100 |
| Vitamin A Palmitate | 0.100 |
| Propylparaben | 0.100 |
| Disodium EDTA | 0.100 |
| L-Lactic Acid | 0.010 |
| Biotin | 0.001 |
| Deionized Water | qs |

EXAMPLE 2

Another skin oil and grease inhibiting creme is prepared having a composition described in Table II.

TABLE II

| COMPONENT | WEIGHT % |
| --- | --- |
| Carbopol 1382 ® (2% Solids) | 18.000 |
| Cyclomethicone | 6.000 |
| Cetyl Alcohol | 4.400 |
| Spectron SA-13 ® (Tridecyl Salicylate) | 4.000 |
| Glycerin | 3.000 |
| Isoarachidyl Neopentanoate | 2.400 |
| Emulgade 1000 NI ® | 1.750 |
| Willowbark Extract | 1.500 |
| Triethanolamine 99% | 1.420 |
| $C_{18}$–$C_{36}$ Fatty Acid | 1.200 |
| BRIJ 721 ® (Vegetable) | 1.200 |
| Arachidyl Behenate | 1.000 |
| Actiglyde-J Special ® | 1.000 |
| Polymethyl Methacrylate | 1.000 |
| Vitamin E Acetate | 1.000 |
| Sodium Pyrolidone Carboxylate (50% solids) | 0.750 |
| Algae Extract | 0.500 |
| DL-Panthenol | 0.500 |
| Silicone 200 (10 cst) | 0.400 |
| $C_{12}$–$C_{20}$ Acid-PEG 8 Esters | 0.400 |
| Microat SF ® | 0.360 |
| Bernel Ester TOC ® | 0.360 |
| Glydant ® | 0.300 |
| Methylparaben | 0.300 |
| BRIJ 72 ® (Vegetable) | 0.300 |
| Polyethylene (A-C 400) ® | 0.300 |
| Shea Butter | 0.200 |
| Disodium EDTA | 0.100 |
| Amigel ® | 0.100 |
| Propylparaben | 0.100 |
| Vitamin A Palmitate | 0.100 |
| L-Lactic Acid | 0.010 |
| Biotin | 0.001 |
| Vitazyme C ® | 0.001 |
| Deionized Water | qs |

EXAMPLE 3

The present Example reports an in vitro analysis of sebum suppression by use of a salicylate ester.

In Vitro Sebocyte Lipogenesis Assay

Human sebaceous glands were isolated from the nose of a male (age 60) and cultured using submerged tissue culture techniques (Bajor et al, *J. Invest. Dermatol.* 102: 1994. P. 564). These sebocytes accumulate intracellular lipid droplets characteristic of mature human sebum.

Harvested and passaged sebocytes were added to each well of a 48 well tissue culture plate and incubated at 37° C. in the presence of 7.5% $CO_2$ for 10 days. The growth medium was changed three times per week. On the day of experimentation, the growth medium was removed and the sebocytes washed three times with phosphate buffered saline (PBS). Fresh PBS in 0.5 ml amount was added to each well and 10 microliters of active agent speculated to inhibit lipogenesis. Triplicate wells were utilized for each sample. Controls consisted of PBS, dimethyl sulfoxide (DMSO) used to solubilize the lipophilic compounds, and phenol red, a compound which possesses estrogen-like activity. The cultures were incubated at 37° C./7.5% $CO_2$ for 30 minutes. Radioactive label was prepared by adding 100 ul of 14-C labelled acetic acid (Amersham, sodium salt, specific activity of 56 mCi/mmol) to 10 ml of 50 mM sodium acetate buffer. Then 50 ul was added to each well containing the sebocytes and active agents. The cultures were returned to the incubator for 4 hours. Thereafter the treatments and label were removed and the sebocytes rinsed three times with fresh PBS. Sebocytes were harvested and 10 microliters removed and set aside for protein assessment. The remaining samples containing the 14-C label were extracted and the label counted using a Beckman scintillation counter. Triplicates were performed for each sample.

For each 48 well tissue culture plate, 16 samples could be analyzed. Of these, 1 sample was reserved for PBS, 1 sample for DMSO, and 1 sample for phenol red leaving 13 remaining samples.

TABLE I

| Tridecylsalicylate Concentration | % Reduction | Standard Deviation |
| --- | --- | --- |
| 0.00003% | 8.5 | 2.5 |
| 0.0003% | 13.3 | 1.0 |
| 0.003% | 28.3 | 2.1 |
| 0.01% | 44.7 | 9.7 |
| 0.03% | 49.1 | 6.3 |
| 0.05% | 48.9 | 8.5 |
| 0.1% | 63.0 | 7.7 |

TABLE II

| Octylsalicylate Conc. | % Reduction | Standard Deviation |
| --- | --- | --- |
| 0.005% | 11.6 | 12.2 |
| 0.01% | 11.6 | 4.1 |
| 0.05% | 22.4 | 15.1 |
| 0.1% | 8.3 | 19.7 |
| 0.5% | 0 | 12.6 |
| 1.0% | 2.2 | 7.8 |
| 0.1% Phenol Red | 40.8 | 12.5 |

TABLE III

| Salicylic Acid conc | % Reduction | Standard Deviation |
| --- | --- | --- |
| 0.00014% | 11.4 | 9.0 |
| 0.0014% | 10.1 | 10.5 |
| 0.014% | 13.1 | 13.4 |
| 0.14% | 3.6 | 7.4 |

Based on the results In Tables I, II and III, it is evident that tridecyl salicylate has significant activity in reducing oiliness and grease, especially compared to octylsalicylate and salicylic acid.

The foregoing description and examples illustrate selected embodiments of the present invention. In light thereof, various modifications will be suggested to one skilled in the art, all of which are within the spirit and purview of this invention.

What is claimed is:

1. A method for inhibiting skin production of oils and grease, the method comprising applying to the skin a safe and effective amount of salicylate ester in a pharmaceutically acceptable carrier, the salicylate ester having the formula (I):

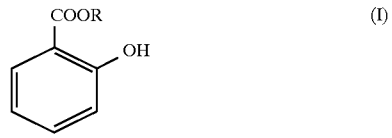

wherein R is a $C_{11}$–$C_{30}$ alkyl or alkenyl radical.

2. The method according to claim 1 wherein R is a $C_{12}$–$C_{20}$ alkyl radical.

3. The method according to claim 1 wherein the salicylate ester is tridecyl salicylate.

* * * * *